United States Patent
Bartrolí Orpí et al.

(10) Patent No.: US 7,589,125 B2
(45) Date of Patent: Sep. 15, 2009

(54) 2,4-DIHYDROXYBENZOIC ACID DERIVATIVES

(75) Inventors: Javier Bartrolí Orpí, Barcelona (ES); Carmen Almansa Rosales, Barcelona (ES); Alberto Fernández De Arriba, Barcelona (ES)

(73) Assignee: Palau Pharma, S.A., Palau-solita i Plegamans (ES)

( * ) Notice: Subject to any disclaimer, the term of this patent is extended or adjusted under 35 U.S.C. 154(b) by 260 days.

(21) Appl. No.: 10/521,461

(22) PCT Filed: Jul. 17, 2003

(86) PCT No.: PCT/EP03/07777

§ 371 (c)(1), (2), (4) Date: Jan. 18, 2005

(87) PCT Pub. No.: WO2004/009528

PCT Pub. Date: Jan. 29, 2004

(65) Prior Publication Data

US 2005/0267205 A1    Dec. 1, 2005

(30) Foreign Application Priority Data

Jul. 18, 2002    (ES)    ................................ 2002501826

(51) Int. Cl.
*A61K 31/235*    (2006.01)
*C07C 59/11*    (2006.01)
*C07C 69/025*    (2006.01)

(52) U.S. Cl. .................... 514/544; 560/55; 562/465

(58) Field of Classification Search ................. 514/544; 560/55; 562/465
See application file for complete search history.

(56) References Cited

U.S. PATENT DOCUMENTS

| 3,766,247 A | 10/1973 | Mendel |
| 4,871,769 A | 10/1989 | Fedeli et al. |
| 4,960,884 A | 10/1990 | Roush et al. |
| 5,374,772 A | 12/1994 | Carson et al. |
| 5,488,135 A | 1/1996 | Nussbaumer et al. |

FOREIGN PATENT DOCUMENTS

| EP | 601385 | 6/1994 |
| EP | 337176 | 12/1994 |

OTHER PUBLICATIONS

Arnold-Stanton, R. et al., Tandem Nucleophilic Additions of Aryloxides, *Journal of Organic Chemistry*, 1991, pp. 151-157, vol. 56, No. 1. American Chemical Society.

Hardcastle, I.R. et al., Inhibition of Protein Prenylation by Metabolites of Limonene, *Biochemical Pharmacology*, 1999, pp. 801-809, vol. 57. Elsevier.

Hardcastle, I.R. et al., "Polymer-assisted solution-phase library synthesis of 4-alkoxy-2-hydroxy-3,5,6-trifluorobenzoic acids," *Tetrahedron Letters*, 2001, pp. 1363-1365, vol. 42, No. 7. Pergamon.

Mu, J. et al., "Synthesis and monolayer formation of liquid crystal polysiloxanes having a lateral side chain with a perfluoroalkyl chain," *Colloids and Surfaces A: Physicochemical and Engineering Aspects*, 2001, pp. 303-313, vol. 181, Elsevier Science Publishers, Amsterdam, NL.

O'Neil, Maryadele J. et al., (Eds), "3285. Dimethyl Sulfoxide," *The Merck Index*, 2001, pp. 3285-3286. Merck & Co., Inc. New York, NY, USA.

*Primary Examiner*—Taofiq A Solola
(74) *Attorney, Agent, or Firm*—Rothwell, Figg, Ernst & Manbeck

(57) ABSTRACT

The present invention relates to novel compounds of formula (I) and to the salts, solvates and prodrugs thereof, wherein the meanings of the various substituents are as disclosed in the description. Said compounds are useful for the treatment or prevention of psoriasis and other immune diseases.

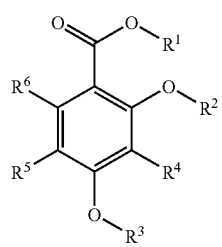

(I)

15 Claims, 2 Drawing Sheets

2,4-DIHYDROXYBENZOIC ACID DERIVATIVES

This application is a 371 filing of PCT/EP2003/007777, filed Jul. 17, 2003 which claims priority from Spanish Application P 200201826, filed Jul. 18, 2002.

FIELD OF THE INVENTION

The present invention relates to a novel series of 2,4-dihydroxybenzoic acid derivatives, as well as to a process for their preparation, to the pharmaceutical compositions comprising them and to their use for the manufacture of medicaments, particularly for the treatment or prevention of psoriasis and other immune diseases.

DESCRIPTION OF THE PRIOR ART

Psoriasis is a chronic inflammatory disease of the skin that affects as much as 2% of the world's population. Patients exhibit epidermal proliferation leading to erythema, scaling and thickening of the skin, which can range from mild to severe. The disease is characterized by the hyperplasia of the skin and the infiltration of T-lymphocytes, monocytes and neutrophils into the epidermis.

Although there are various topical and systemic symptomatic treatments for psoriasis, such as UV light, glucocorticoids, vitamin D analogues, retinoids, tazarotene, methotrexate and cyclosporine, there is still no effective therapy to cure the disease. Furthermore, some of the current treatments are aggressive and cause important side effects.

Thus, there presently exists a need to find novel drugs useful for the treatment of psoriasis. This problem is solved by the 2,4-dihydroxybenzoic acid derivatives of formula I of the present invention.

Some derivatives of 2,4-dihydroxybenzoic acid structurally close to the compounds of the invention have been disclosed in the literature. In particular, in J. Mu et al, *Colloids and surfaces, A: Physicochemical and Engineering Aspects*, 2001, 181, 303-313 the compounds ethyl 2-hydroxy-4-(3,3,4,4,5,5,6,6,6-nonafluorohexyloxy)benzoate, ethyl 2-hydroxy-4-(3,3,4,4,5,5,6,6,7,7,8,8,8-tridecafluorooctyloxy)benzoate and ethyl 4-(3,3,4,4,5,5,6,6,7,7,8,8,9,9,10,10,10-heptadecafluorodecyloxy)-2-hydroxybenzoate are disclosed. These compounds are useful as intermediates in the preparation of liquid crystals. No therapeutical application has been described for these compounds. In R. Arnold-Stanton and D. M. Lemal, *J. Org. Chem.* 1991, 56, 151-157 the compound methyl 2,6-dihydroxy-4-(1,1,2,2-tetrafluoroethoxy)benzoate is described as a by-product in a reaction of 1,3,5-trihydroxybenzene. No therapeutical application has been described for this compound. Finally, in I. R. Hardcastle et al, *Tetrahedron Letters* 2001, 42(7), 1363-1365 the compound 2,3,5-trifluoro-4-(3-fluoropropoxy)-6-hydroxybenzoic acid is disclosed as a potential farnesyltransferase inhibitor, although as mentioned in said article this compound turned out to be inactive; no therapeutical application has been thus described for this compound.

SUMMARY OF THE INVENTION

The present invention is directed to a group of 2,4-dihydroxybenzoic acid derivatives, as well as salts, solvates and prodrugs of these compounds. The compounds can be provided in pharmaceutically effective amounts with at least one pharmaceutically acceptable excipient as a pharmaceutical composition. The compositions can be administered for the treatment or prevention of immune diseases and cancer.

DETAILED DESCRIPTION OF THE INVENTION

Figure 1:
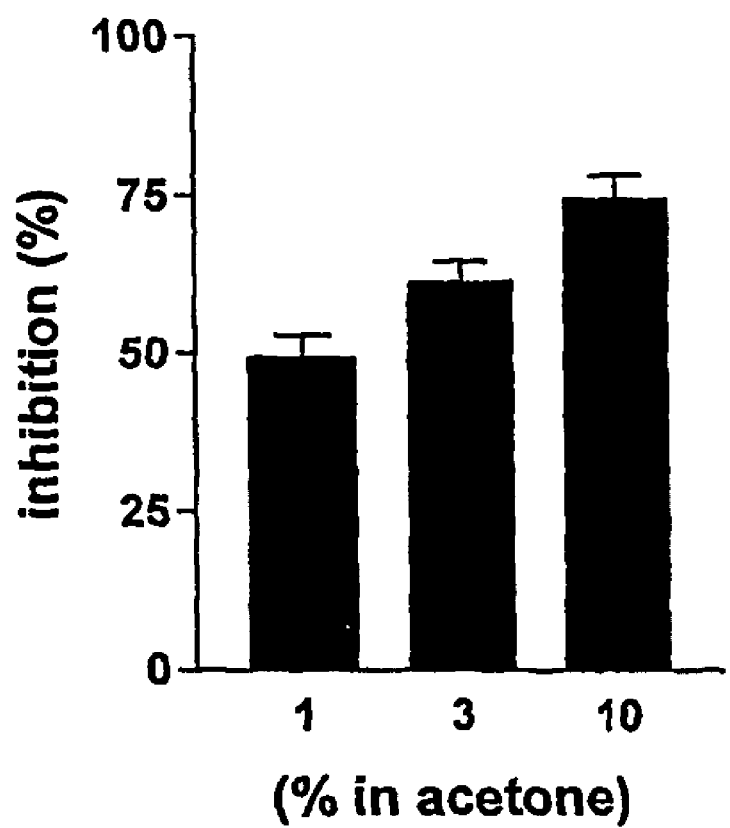
FIG. 1 is a bar chart showing the results obtained with the compound of Example 6 in the oxazalone-induced delayed hypersensitivity test (Test 1)

One aspect of the present invention relates to the novel compounds of general formula I:

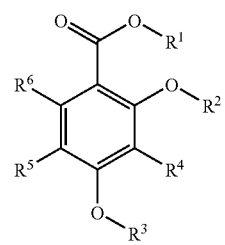

wherein:
$R^1$ represents hydrogen or $C_{1-4}$ alkyl;
$R^2$ represents hydrogen or $-C(=O)R^7$;
$R^3$ represents $C_{1-5}$ fluoroalkyl, $C_{2-5}$ fluoroalkenyl or $C_{2-5}$ fluoroalkynyl;
$R^4$, $R^5$ and $R^6$ independently represent hydrogen, $C_{1-4}$ alkyl, $C_{1-4}$ haloalkyl, $C_{1-4}$ alkoxy, $C_{1-4}$ haloalkoxy, halogen, cyano, hydroxy, nitro, $-NR^8R^9$, $-S(O)_xR^{10}$ or $-C(=O)R^{11}$;
$R^7$ and $R^{10}$ independently represent $C_{1-4}$ alkyl;
$R^8$, $R^9$ and $R^{11}$ independently represent hydrogen or $C_{1-4}$ alkyl; and
x represents 0, 1 or 2;

with the proviso that when $R^1$ represents methyl, $R^2$ represents hydrogen, $R^3$ represents 1,1,2,2-tetrafluoroethyl and $R^4$ and $R^5$ represent hydrogen then $R^6$ cannot be hydroxy, and with the further proviso that when $R^1$ represents hydrogen, $R^2$ represents hydrogen and $R^3$ represents 3-fluoropropyl then $R^4$, $R^5$ and $R^6$ cannot represent simultaneously fluoro.

A further aspect of the invention relates to a compound of general formula I:

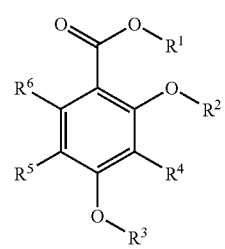

wherein:

$R^1$ represents hydrogen or $C_{1-4}$ alkyl;
$R^2$ represents hydrogen or —C(=O)$R^7$;
$R^3$ represents $C_{1-5}$ fluoroalkyl, $C_{2-5}$ fluoroalkenyl or $C_{2-5}$ fluoroalkynyl;
$R^4$, $R^5$ and $R^6$ independently represent hydrogen, $C_{1-4}$ alkyl, $C_{1-4}$ haloalkyl, $C_{1-4}$ alkoxy, $C_{1-4}$ haloalkoxy, halogen, cyano, hydroxy, nitro, —NR$^8$R$^9$, —S(O)$_x$R$^{10}$ or —C(=O)R$^{11}$;
$R^7$ and $R^{10}$ independently represent $C_{1-4}$ alkyl;
$R^8$, $R^9$ and $R^{11}$ independently represent hydrogen or $C_{1-4}$ alkyl; and
x represents 0, 1 or 2;

for use as an active pharmaceutical ingredient.

A further aspect of the invention relates to a compound of general formula I:

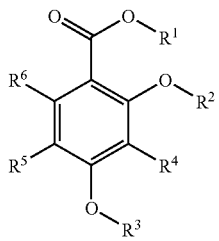

wherein:

$R^1$ represents hydrogen or $C_{1-4}$ alkyl;
$R^2$ represents hydrogen or —C(=O)$R^7$;
$R^3$ represents $C_{1-5}$ fluoroalkyl, $C_{2-5}$ fluoroalkenyl or $C_{2-5}$ fluoroalkynyl;
$R^4$, $R^5$ and $R^6$ independently represent hydrogen, $C_{1-4}$ alkyl, $C_{1-4}$ haloalkyl, $C_{1-4}$ alkoxy, $C_{1-4}$ haloalkoxy, halogen, cyano, hydroxy, nitro, —NR$^8$R$^9$, —S(O)$_x$R$^{10}$ or —C(=O)R$^{11}$;
$R^7$ and $R^{10}$ independently represent $C_{1-4}$ alkyl;
$R^8$, $R^9$ and $R^{11}$ independently represent hydrogen or $C_{1-4}$ alkyl; and
x represents 0, 1 or 2;

for use in a method of treatment of the human or animal body.

The present invention also relates to the salts of the compounds of the invention as well as to their solvates and prodrugs. The term prodrug means any compound which releases a compound of formula I in vivo when such prodrug is administered to a mammalian subject.

Some compounds of formula I can have chiral centres, which can give rise to various stereoisomers. The present invention relates to each one of the individual stereoisomers as well as to their mixtures. Moreover, some of the compounds of the present invention can show cis/trans isomery. The present invention relates to each one of the geometric isomers as well as to their mixtures.

The compounds of formula I disclosed in the present invention have shown very good activity in animal models for psoriasis. Likewise, these compounds have shown good activity in pharmacological models of immunomodulation, for example they have been proved to inhibit T-lymphocyte proliferation, and therefore they may be useful for the treatment or prevention of other immune diseases as well. The compounds of formula I have further been shown to induce apoptosis in cancer cells and may thus also be useful for the treatment or prevention of cancer. Furthermore, the compounds of the present invention exhibit a good safety profile.

Therefore, a further aspect of the present invention relates to the pharmaceutical compositions which comprise an effective amount of a compound of formula I

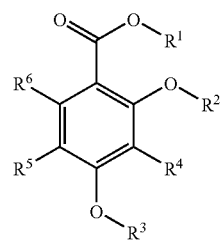

wherein:

$R^1$ represents hydrogen or $C_{1-4}$ alkyl;
$R^2$ represents hydrogen or —C(=O)$R^7$;
$R^3$ represents $C_{1-5}$ fluoroalkyl, $C_{2-5}$ fluoroalkenyl or $C_{2-5}$ fluoroalkynyl;
$R^4$, $R^5$ and $R^6$ independently represent hydrogen, $C_{1-4}$ alkyl, $C_{1-4}$ haloalkyl, $C_{1-4}$ alkoxy, $C_{1-4}$ haloalkoxy, halogen, cyano, hydroxy, nitro, —NR$^8$R$^9$, —S(O)$_x$R$^{10}$ or —C(=O)R$^{11}$;
$R^7$ and $R^{10}$ independently represent $C_{1-4}$ alkyl;
$R^8$, $R^9$ and $R^{11}$ independently represent hydrogen or $C_{1-4}$ alkyl; and
x represents 0, 1 or 2;

or a pharmaceutically acceptable salt, solvate or prodrug thereof and one or more pharmaceutically acceptable excipients.

A further aspect of the present invention relates to the use of a compound of formula I

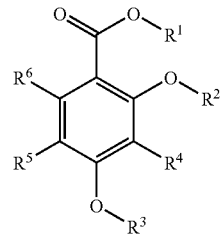

wherein:

$R^1$ represents hydrogen or $C_{1-4}$ alkyl;
$R^2$ represents hydrogen or —C(=O)$R^7$;
$R^3$ represents $C_{1-5}$ fluoroalkyl, $C_{2-5}$ fluoroalkenyl or $C_{2-5}$ fluoroalkynyl;
$R^4$, $R^5$ and $R^6$ independently represent hydrogen, $C_{1-4}$ alkyl, $C_{1-4}$ haloalkyl, $C_{1-4}$ alkoxy, $C_{1-4}$ haloalkoxy, halogen, cyano, hydroxy, nitro, —NR$^8$R$^9$, —S(O)$_x$R$^{10}$ or —C(=O)R$^{11}$;
$R^7$ and $R^{10}$ independently represent $C_{1-4}$ alkyl;
$R^8$, $R^9$ and $R^{11}$ independently represent hydrogen or $C_{1-4}$ alkyl; and
x represents 0, 1 or 2;

or a pharmaceutically acceptable salt, solvate or prodrug thereof for the manufacture of a medicament for the treatment or prevention of immune diseases. In a preferred embodiment, such immune disease is selected from the group consisting of psoriasis, other skin diseases such as atopic dermatitis, contact dermatitis, lichen planus, dermatomyositis, scleroderma, erythema multiform, urticaria and pemphigus, inflammatory bowel disease including Crohn's disease and ulcerative colitis, rheumatoid arthritis and other arthritic diseases such as gouty arthritis, psoriatic arthritis, juvenile arthritis and ankylosing spondylitis, multiple sclerosis and other autoimmune neuropathies, diabetes, transplant rejection, graft-versus-host disease, lupus erythematosus, vasculitis, Sjögren's syndrome, Guillain-Barre syndrome, glomerulonephritis, respiratory diseases such as allergic rhinitis, asthma, fibrosis and chronic obstructive pulmonary disease, and neoplasias with proliferation of immune cells.

A further aspect of the present invention relates to the use of a compound of formula I

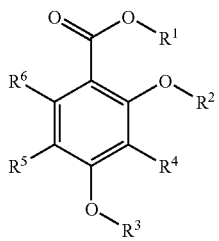

wherein:
$R^1$ represents hydrogen or $C_{1-4}$ alkyl;
$R^2$ represents hydrogen or —C(=O)$R^7$;
$R^3$ represents $C_{1-5}$ fluoroalkyl, $C_{2-5}$ fluoroalkenyl or $C_{2-5}$ fluoroalkynyl;
$R^4$, $R^5$ and $R^6$ independently represent hydrogen, $C_{1-4}$ alkyl, $C_{1-4}$ haloalkyl, $C_{1-4}$ alkoxy, $C_{1-4}$ haloalkoxy, halogen, cyano, hydroxy, nitro, —NR$^8$R$^9$, —S(O)$_x$R$^{10}$ or —C(=O)R$^{11}$;
$R^7$ and $R^{10}$ independently represent $C_{1-4}$ alkyl;
$R^8$, $R^9$ and $R^{11}$ independently represent hydrogen or $C_{1-4}$ alkyl; and
x represents 0, 1 or 2;

or a pharmaceutically acceptable salt, solvate or prodrug thereof for the manufacture of a medicament for the treatment or prevention of cancer.

A further aspect of the present invention relates to a compound of formula I

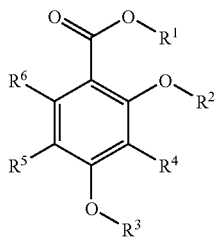

wherein:
$R^1$ represents hydrogen or $C_{1-4}$ alkyl;
$R^2$ represents hydrogen or —C(=O)$R^7$;
$R^3$ represents $C_{1-5}$ fluoroalkyl, $C_{2-5}$ fluoroalkenyl or $C_{2-5}$ fluoroalkynyl;
$R^4$, $R^5$ and $R^6$ independently represent hydrogen, $C_{1-4}$ alkyl, $C_{1-4}$ haloalkyl, $C_{1-4}$ alkoxy, $C_{1-4}$ haloalkoxy, halogen, cyano, hydroxy, nitro, —NR$^8$R$^9$, —S(O)$_x$R$^{10}$ or —C(=O)R$^{11}$;
$R^7$ and $R^{10}$ independently represent $C_{1-4}$ alkyl;
$R^8$, $R^9$ and $R^{11}$ independently represent hydrogen or $C_{1-4}$ alkyl; and
x represents 0, 1 or 2;

or a pharmaceutically acceptable salt, solvate or prodrug thereof for the treatment or prevention of immune diseases. In a preferred embodiment, such immune disease is selected from the group consisting of psoriasis, other skin diseases such as atopic dermatitis, contact dermatitis, lichen planus, dermatomyositis, scleroderma, erythema multiform, urticaria and pemphigus, inflammatory bowel disease including Crohn's disease and ulcerative colitis, rheumatoid arthritis and other arthritic diseases such as gouty arthritis, psoriatic arthritis, juvenile arthritis and ankylosing spondylitis, multiple sclerosis and other autoimmune neuropathies, diabetes, transplant rejection, graft-versus-host disease, lupus erythematosus, vasculitis, Sjögren's syndrome, Guillain-Barre syndrome, glomerulonephritis, respiratory diseases such as allergic rhinitis, asthma, fibrosis and chronic obstructive pulmonary disease, and neoplasias with proliferation of immune cells.

A further aspect of the present invention relates to a compound of formula I

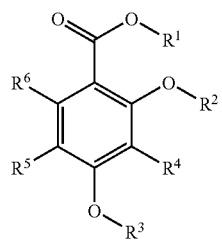

wherein:
$R^1$ represents hydrogen or $C_{1-4}$ alkyl;
$R^2$ represents hydrogen or —C(=O)$R^7$;
$R^3$ represents $C_{1-5}$ fluoroalkyl, $C_{2-5}$ fluoroalkenyl or $C_{2-5}$ fluoroalkynyl;
$R^4$, $R^5$ and $R^6$ independently represent hydrogen, $C_{1-4}$ alkyl, $C_{1-4}$ haloalkyl, $C_{1-4}$ alkoxy, $C_{1-4}$ haloalkoxy, halogen, cyano, hydroxy, nitro, —NR$^8$R$^9$, —S(O)$_x$R$^{10}$ or —C(=O)R$^{11}$;
$R^7$ and $R^{10}$ independently represent $C_{1-4}$ alkyl;
$R^8$, $R^9$ and $R^{11}$ independently represent hydrogen or $C_{1-4}$ alkyl; and
x represents 0, 1 or 2;

or a pharmaceutically acceptable salt, solvate or prodrug thereof for the treatment or prevention of cancer.

A further aspect of the present invention relates to the use of a compound of formula I

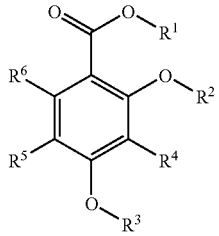

wherein:
$R^1$ represents hydrogen or $C_{1-4}$ alkyl;
$R^2$ represents hydrogen or —C(=O)$R^7$;
$R^3$ represents $C_{1-5}$ fluoroalkyl, $C_{2-5}$ fluoroalkenyl or $C_{2-5}$ fluoroalkynyl;
$R^4$, $R^5$ and $R^6$ independently represent hydrogen, $C_{1-4}$ alkyl, $C_{1-4}$ haloalkyl, $C_{1-4}$ alkoxy, $C_{1-4}$ haloalkoxy, halogen, cyano, hydroxy, nitro, —$NR^8R^9$, —$S(O)_xR^{10}$ or —C(=O)$R^{11}$;
$R^7$ and $R^{10}$ independently represent $C_{1-4}$ alkyl;
$R^8$, $R^9$ and $R^{11}$ independently represent hydrogen or $C_{1-4}$ alkyl; and
x represents 0, 1 or 2;

or a pharmaceutically acceptable salt, solvate or prodrug thereof for the treatment or prevention of immune diseases. In a preferred embodiment, such immune disease is selected from the group consisting of psoriasis, other skin diseases such as atopic dermatitis, contact dermatitis, lichen planus, dermatomyositis, scleroderma, erythema multiform, urticaria and pemphigus, inflammatory bowel disease including Crohn's disease and ulcerative colitis, rheumatoid arthritis and other arthritic diseases such as gouty arthritis, psoriatic arthritis, juvenile arthritis and ankylosing spondylitis, multiple sclerosis and other autoimmune neuropathies, diabetes, transplant rejection, graft-versus-host disease, lupus erythematosus, vasculitis, Sjögren's syndrome, Guillain-Barre syndrome, glomerulonephritis, respiratory diseases such as allergic rhinitis, asthma, fibrosis and chronic obstructive pulmonary disease, and neoplasias with proliferation of immune cells.

A further aspect of the present invention relates to the use of a compound of formula I

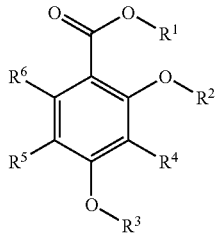

wherein:
$R^1$ represents hydrogen or $C_{1-4}$ alkyl;
$R^2$ represents hydrogen or —C(=O)$R^7$;
$R^3$ represents $C_{1-5}$ fluoroalkyl, $C_{2-5}$ fluoroalkenyl or $C_{2-5}$ fluoroalkynyl;
$R^4$, $R^5$ and $R^6$ independently represent hydrogen, $C_{1-4}$ alkyl, $C_{1-4}$ haloalkyl, $C_{1-4}$ alkoxy, $C_{1-4}$ haloalkoxy, halogen, cyano, hydroxy, nitro, —$NR^8R^9$, —$S(O)_xR^{10}$ or —C(=O)$R^{11}$;
$R^7$ and $R^{10}$ independently represent $C_{1-4}$ alkyl;
$R^8$, $R^9$ and $R^{11}$ independently represent hydrogen or $C_{1-4}$ alkyl; and
x represents 0, 1 or 2;

or a pharmaceutically acceptable salt, solvate or prodrug thereof for the treatment or prevention of cancer.

A further aspect of the present invention relates to a method of treating or preventing an immune disease in a mammal in need thereof, especially a human being, which comprises administering to said mammal a therapeutically effective amount of a compound of formula I

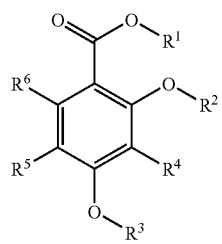

wherein:
$R^1$ represents hydrogen or $C_{1-4}$ alkyl;
$R^2$ represents hydrogen or —C(=O)$R^7$;
$R^3$ represents $C_{1-5}$ fluoroalkyl, $C_{2-5}$ fluoroalkenyl or $C_{2-5}$ fluoroalkynyl;
$R^4$, $R^5$ and $R^6$ independently represent hydrogen, $C_{1-4}$ alkyl $C_{1-4}$ haloalkyl, $C_{1-4}$ alkoxy, $C_{1-4}$ haloalkoxy, halogen, cyano, hydroxy, nitro, —$NR^8R^9$, —$S(O)_xR^{10}$ or —C(=O)$R^{11}$;
$R^7$ and $R^{10}$ independently represent $C_{1-4}$ alkyl;
$R^8$, $R^9$ and $R^{11}$ independently represent hydrogen or $C_{1-4}$ alkyl; and
x represents 0, 1 or 2;

or a pharmaceutically acceptable salt, solvate or prodrug thereof. In a preferred embodiment, such immune disease is selected from the group consisting of psoriasis, other skin diseases such as atopic dermatitis, contact dermatitis, lichen planus, dermatomyositis, scleroderma, erythema multiform, urticaria and pemphigus, inflammatory bowel disease including Crohn's disease and ulcerative colitis, rheumatoid arthritis and other arthritic diseases such as gouty arthritis, psoriatic arthritis, juvenile arthritis and ankylosing spondylitis, multiple sclerosis and other autoimmune neuropathies, diabetes, transplant rejection, graft-versus-host disease, lupus erythematosus, vasculitis, Sjögren's syndrome, Guillain-Barre syndrome, glomerulonephritis, respiratory diseases such as allergic rhinitis, asthma, fibrosis and chronic obstructive pulmonary disease, and neoplasias with proliferation of immune cells.

A further aspect of the present invention relates to a method of treating or preventing cancer in a mammal in need thereof, especially a human being, which comprises administering to said mammal a therapeutically effective amount of a compound of formula I

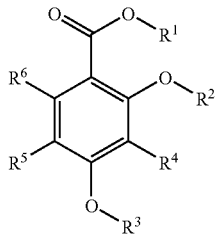

wherein:

$R^1$ represents hydrogen or $C_{1-4}$ alkyl;

$R^2$ represents hydrogen or —C(=O)$R^7$;

$R^3$ represents $C_{1-5}$ fluoroalkyl, $C_{2-5}$ fluoroalkenyl or $C_{2-5}$ fluoroalkynyl;

$R^4$, $R^5$ and $R^6$ independently represent hydrogen, $C_{1-4}$ alkyl, $C_{1-4}$ haloalkyl, $C_{1-4}$ alkoxy, $C_{1-4}$ haloalkoxy, halogen, cyano, hydroxy, nitro, —NR$^8$R$^9$, —S(O)$_x$R$^{10}$, or —C(=O)R$^{11}$;

$R^7$ and $R^{10}$ independently represent $C_{1-4}$ alkyl;

$R^8$, $R^9$ and $R^{11}$ independently represent hydrogen or $C_{1-4}$ alkyl; and x represents 0, 1 or 2;

or a pharmaceutically acceptable salt, solvate or prodrug thereof.

A further aspect of the present invention relates to a process for preparing a compound of formula I,

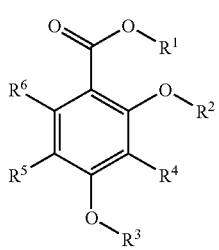

wherein:

$R^1$ represents hydrogen or $C_{1-4}$ alkyl;

$R^2$ represents hydrogen or —C(=O)$R^7$;

$R^3$ represents $C_{1-5}$ fluoroalkyl, $C_{2-5}$ fluoroalkenyl or $C_{2-5}$ fluoroalkynyl;

$R^4$, $R^5$ and $R^6$ independently represent hydrogen, $C_{1-4}$ alkyl, $C_{1-4}$ haloalkyl, $C_{1-4}$ alkoxy, $C_{1-4}$ haloalkoxy, halogen, cyano, hydroxy, nitro, —NR$^8$R$^9$, —S(O)$_x$R$^{10}$ or —C(=O)R$^{11}$;

$R^7$ and $R^{10}$ independently represent $C_{1-4}$ alkyl;

$R^8$, $R^9$ and $R^{11}$ independently represent hydrogen or $C_{1-4}$ alkyl; and x represents 0, 1 or 2;

which comprises:

(a) reacting a phenol of formula II

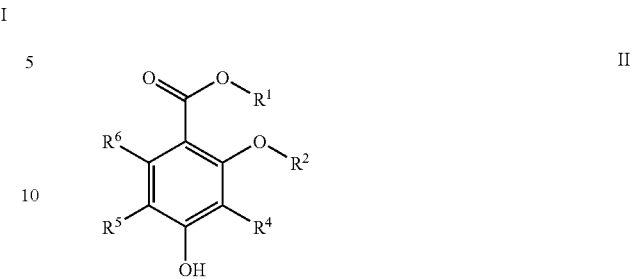

wherein $R^1$, $R^2$, $R^4$, $R^5$ and $R^6$ have the meaning described above, with an alkylating agent of formula G-$R^3$ (III), wherein $R^3$ has the meaning described above and G represents a leaving group; or (b) converting, in one or more steps, a compound of formula I into another compound of formula I; and (c) if desired, after the above steps and when $R^1$ and/or $R^2$ represent hydrogen, reacting a compound of formula I with a base, to obtain the corresponding addition salt.

In the above definitions, and unless otherwise stated, the term $C_{1-n}$ alkyl, as a group or part of a group, means a lineal or branched alkyl group containing from 1 to n carbon atoms. When n is 4, it includes the groups methyl, ethyl, propyl, isopropyl, butyl, isobutyl, sec-butyl, and tert-butyl. When n is 5, it includes in addition the groups pentyl, 1-methylbutyl, 2-methylbutyl, 3-methylbutyl, 1-ethylpropyl, 2-ethylpropyl and 1,2-dimethylpropyl.

A $C_{2-5}$ alkenyl group means a lineal or branched alkyl group containing from 2 to 5 carbon atoms and containing one or more double bonds.

A $C_{2-5}$ alkynyl group means a lineal or branched alkyl group containing from 2 to 5 carbon atoms and containing one or more triple bonds.

A $C_{1-4}$ alkoxy group means a group of formula "$C_{1-4}$ alkyl-O—" and it includes the groups methoxy, ethoxy, propoxy, isopropoxy, butoxy, isobutoxy, sec-butoxy, and tert-butoxy.

The term halogen or its abbreviation halo means fluoro, chloro, bromo or iodo.

A $C_{1-4}$ haloalkyl group means a group resulting from the replacement of one or more hydrogen atoms of a $C_{1-4}$ alkyl group with one or more halogen atoms (that is, fluoro, chloro, bromo or iodo), which can be the same or different. Examples include, among others, trifluoromethyl, fluoromethyl, 1-chloroethyl, 2-chloroethyl, 1-fluoroethyl, 2-fluoroethyl, 1-bromoethyl, 2-bromoethyl, 2-iodoethyl, 2,2-difluoroethyl, 2,2,2-trifluoroethyl, pentafluoroethyl, 3-fluoropropyl, 3-chloropropyl, 3,3,3-trifluoropropyl, 2,2,3,3-tetrafluoropropyl, 2,2,3,3,3-pentafluoropropyl, heptafluoropropyl, 4-fluorobutyl, 4-chlorobutyl and nonafluorobutyl.

A $C_{1-4}$ haloalkoxy group means a group resulting from the replacement of one or more hydrogen atoms of a $C_{1-4}$ alkoxy group with one or more halogen atoms (that is, fluoro, chloro, bromo or iodo), which can be the same or different. Examples include, among others, trifluoromethoxy, fluoromethoxy, 1-chloroethoxy, 2-chloroethoxy, 1-fluoroethoxy, 2-fluoroethoxy, 1-bromoethoxy, 2-bromoethoxy, 2-iodoethoxy, 2,2-difluoroethoxy, 2,2,2-trifluoroethoxy, pentafluoroethoxy, 3-fluoropropoxy, 3-chloropropoxy, 3,3,3-trifluoropropoxy, 2,2,3,3-tetrafluoropropoxy, 2,2,3,3,3-pentafluoropropoxy, heptafluoropropoxy, 4-fluorobutoxy, 4-chlorobutoxy and nonafluorobutoxy.

A $C_{1-5}$ fluoroalkyl group means a $C_{1-5}$ alkyl group, as defined above, wherein one or more hydrogen atoms are replaced with one or more fluorine atoms, including the possibility that all the hydrogen atoms are replaced with fluorine atoms. Examples include, among others, trifluoromethyl, fluoromethyl, 1-fluoroethyl, 2-fluoroethyl, 2,2-difluoroethyl, 2,2,2-trifluoroethyl, pentafluoroethyl, 3-fluoropropyl, 3,3,3-trifluoropropyl, 2,2,3,3-tetrafluoropropyl, 2,2,3,3,3-pentafluoropropyl, heptafluoropropyl, 4-fluorobutyl, 4,4,4-trifluorobutyl, 3,3,4,4,4-pentafluorobutyl, nonafluorobutyl and 5-fluoropentyl. A $C_{2-5}$ fluoroalkenyl or $C_{2-5}$ fluoroalkynyl group represents a $C_{2-5}$ alkenyl or a $C_{2-5}$ alkynyl group, respectively, wherein one or more hydrogen atoms are replaced with one or more fluorine atoms, including the possibility that all the hydrogen atoms are replaced with fluorine atoms. Examples thereof include the corresponding insaturated radicals of the groups cited above as examples for $C_{1-5}$ fluoroalkyl, for instance 2,3,3-trifluoropropen-2-yl.

Although the present invention includes all the compounds mentioned above, those compounds of formula I wherein $R^1$ represents hydrogen are preferred.

Also preferred are those compounds of formula I wherein $R^2$ represents hydrogen or acetyl (that is, a —C(=O)CH$_3$ group).

Also preferred are those compounds of formula I wherein $R^3$ represents $C_{1-5}$ fluoroalkyl, of which those compounds of formula I wherein $R^3$ represents $C_{1-3}$ fluoroalkyl are more preferred. A particularly preferred class of compounds are those compounds of formula I wherein $R^3$ represents a 2,2,3,3,3-pentafluoropropyl group.

Also preferred are those compounds of formula I wherein $R^4$, $R^5$ and $R^6$ represent hydrogen.

Accordingly, a preferred embodiment of the present invention are the compounds of formula I wherein:
$R^1$ represents hydrogen or $C_{1-4}$ alkyl;
$R^2$ represents hydrogen or —C(=O)$R^7$;
$R^3$ represents $C_{1-5}$ fluoroalkyl, $C_{2-5}$ fluoroalkenyl or $C_{2-5}$ fluoroalkynyl;
$R^4$, $R^5$ and $R^6$ represent hydrogen; and
$R^7$ represents $C_{1-4}$ alkyl;

and the salts, solvates and prodrugs thereof.

Another preferred embodiment of the present invention are the compounds of formula I wherein:
$R^1$ represents hydrogen or $C_{1-4}$ alkyl;
$R^2$ represents hydrogen or —C(=O)$R^7$;
$R^3$ represents $C_{1-5}$ fluoroalkyl;
$R^4$, $R^5$ and $R^6$ independently represent hydrogen, $C_{1-4}$ alkyl, $C_{1-4}$ haloalkyl, $C_{1-4}$ alkoxy, $C_{1-4}$ haloalkoxy, halogen, cyano, hydroxy, nitro, —NR$^8$R$^9$, —S(O)$_x$R$^{10}$ or —C(=O)R$^{11}$;
$R^7$ and $R^{10}$ independently represent $C_{1-4}$ alkyl;
$R^8$, $R^9$ and $R^{11}$ independently represent hydrogen or $C_{1-4}$ alkyl; and
x represents 0, 1 or 2;

with the proviso that when $R^1$ represents methyl, $R^2$ represents hydrogen, $R^3$ represents 1,1,2,2-tetrafluoroethyl and $R^4$ and $R^5$ represent hydrogen then $R^6$ cannot be hydroxy, and with the further proviso that when $R^1$ represents hydrogen, $R^2$ represents hydrogen and $R^3$ represents 3-fluoropropyl then $R^4$, $R^5$ and $R^6$ cannot represent simultaneously fluoro;

and the salts, solvates and prodrugs thereof.

Another preferred embodiment of the present invention are the compounds of formula I wherein:
$R^1$ represents hydrogen or $C_{1-4}$ alkyl;
$R^2$ represents hydrogen or —C(=O)$R^7$;
$R^3$ represents $C_{1-5}$ fluoroalkyl;
$R^4$, $R^5$ and $R^6$ represent hydrogen; and
$R^7$ represents $C_{1-4}$ alkyl;

and the salts, solvates and prodrugs thereof.

Another preferred embodiment of the present invention are the compounds of formula I wherein:
$R^1$ represents hydrogen or $C_{1-4}$ alkyl;
$R^2$ represents hydrogen or —C(=O)$R^7$;
$R^3$ represents $C_{1-3}$ fluoroalkyl, $C_{2-3}$ fluoroalkenyl or $C_{2-3}$ fluoroalkynyl;
$R^4$, $R^5$ and $R^6$ independently represent hydrogen, $C_{1-4}$ alkyl; $C_{1-4}$ haloalkyl, $C_{1-4}$ alkoxy, $C_{1-4}$ haloalkoxy, halogen, cyano, hydroxy, nitro, —NR$^8$R$^9$, —S(O)$_x$R$^{10}$ or —C(=O)R$^{11}$;
$R^7$ and $R^{10}$ independently represent $C_{1-4}$ alkyl;
$R^8$, $R^9$ and $R^{11}$ independently represent hydrogen or $C_{1-4}$ alkyl; and
x represents 0, 1 or 2;

with the proviso that when $R^1$ represents methyl, $R^2$ represents hydrogen, $R^3$ represents 1,1,2,2-tetrafluoroethyl and $R^4$ and $R^5$ represent hydrogen then $R^6$ cannot be hydroxy, and with the further proviso that when $R^1$ represents hydrogen, $R^2$ represents hydrogen and $R^3$ represents 3-fluoropropyl then $R^4$, $R^5$ and $R^6$ cannot represent simultaneously fluoro;

and the salts, solvates and prodrugs thereof.

Another preferred embodiment of the present invention are the compounds of formula I wherein:
$R^1$ represents hydrogen or $C_{1-4}$ alkyl;
$R^2$ represents hydrogen or —C(=O)$R^7$;
$R^3$ represents $C_{1-3}$ fluoroalkyl, $C_{2-3}$ fluoroalkenyl or $C_{2-3}$ fluoroalkynyl;
$R^4$, $R^5$ and $R^6$ represent hydrogen; and
$R^7$ represents $C_{1-4}$ alkyl;

and the salts, solvates and prodrugs thereof.

Another preferred embodiment of the present invention are the compounds of formula I wherein:
$R^1$ represents hydrogen or $C_{1-4}$ alkyl;
$R^2$ represents hydrogen or —C(=O)$R^7$;
$R^3$ represents $C_{1-3}$ fluoroalkyl;
$R^4$, $R^5$ and $R^6$ independently represent hydrogen, $C_{1-4}$ alkyl, $C_{1-4}$ haloalkyl, $C_{1-4}$ alkoxy, $C_{1-4}$ haloalkoxy, halogen, cyano, hydroxy, nitro, —NR$^8$R$^9$, —S(O)$_x$R$^{10}$ or —C(=O)R$^{11}$;
$R^7$ and $R^{10}$ independently represent $C_{1-4}$ alkyl;
$R^8$, $R^9$ and $R^{11}$ independently represent hydrogen or $C_{1-4}$ alkyl; and
x represents 0, 1 or 2;

with the proviso that when $R^1$ represents methyl, $R^2$ represents hydrogen, $R^3$ represents 1,1,2,2-tetrafluoroethyl and $R^4$ and $R^5$ represent hydrogen then $R^6$ cannot be hydroxy, and with the further proviso that when $R^1$ represents hydrogen, $R^2$ represents hydrogen and $R^3$ represents 3-fluoropropyl then $R^4$, $R^5$ and $R^6$ cannot represent simultaneously fluoro;

and the salts, solvates and prodrugs thereof.

Another preferred embodiment of the present invention are the compounds of formula I wherein:
$R^1$ represents hydrogen or $C_{1-4}$ alkyl;
$R^2$ represents hydrogen or —C(=O)$R^7$;
$R^3$ represents $C_{1-3}$ fluoroalkyl;
$R^4$, $R^5$ and $R^6$ represent hydrogen; and
$R^7$ represents $C_{1-4}$ alkyl;

and the salts, solvates and prodrugs thereof.

Another preferred embodiment of the present invention are the compounds of formula I wherein:
$R^1$ represents hydrogen or $C_{1-4}$ alkyl;
$R^2$ represents hydrogen or —C(=O)$R^7$;
$R^3$ represents 2,2,3,3,3-pentafluoropropyl;
$R^4$, $R^5$ and $R^6$ independently represent hydrogen, $C_{1-4}$ alkyl, $C_{1-4}$ haloalkyl, $C_{1-4}$ alkoxy, $C_{1-4}$ haloalkoxy, halogen, cyano, hydroxy, nitro, —NR$^8$R$^9$, —S(O)$_x$R$^{10}$ or —C(=O)R$^{11}$;
$R^7$ and $R^{10}$ independently represent $C_{1-4}$ alkyl;
$R^8$, $R^9$ and $R^{11}$ independently represent hydrogen or $C_{1-4}$ alkyl; and
x represents 0, 1 or 2;

and the salts, solvates and prodrugs thereof.

Another preferred embodiment of the present invention are the compounds of formula I wherein:
$R^1$ represents hydrogen or $C_{1-4}$ alkyl;
$R^2$ represents hydrogen or —C(=O)$R^7$;
$R^3$ represents 2,2,3,3,3-pentafluoropropyl;
$R^4$, $R^5$ and $R^6$ represent hydrogen; and
$R^7$ represents $C_{1-4}$ alkyl;

and the salts, solvates and prodrugs thereof.

In a particularly preferred embodiment of the present invention, $R^1$, $R^2$, $R^4$, $R^5$ and $R^6$ represent hydrogen and $R^3$ represents 2,2,3,3,3-pentafluoropropyl, that is, the compound of formula I is 2-hydroxy-4-(2,2,3,3,3-pentafluoropropoxy)benzoic acid and the salts, solvates and prodrugs thereof.

In another particularly preferred embodiment of the present invention, $R^1$, $R^4$, $R^5$ and $R^6$ represent hydrogen, $R^2$ represents acetyl and $R^3$ represents 2,2,3,3,3-pentafluoropropyl, that is, the compound of formula I is 2-acetoxy-4(2,2,3,3,3-pentafluoropropoxy)benzoic acid and the salts, solvates and prodrugs thereof.

The compounds of the present invention may contain an acidic proton and, consequently, they can form salts with organic as well as inorganic bases, which are also included in the present invention. There is no limitation on the nature of these salts, provided that when used for therapeutic purposes they are pharmaceutically acceptable. Examples of said salts include salts with pharmaceutically acceptable amines like ammonia, alkylamines, hydroxyalkylamines, lysine, arginine, N-methylglucamine, procaine and the like, and salts with inorganic cations such as sodium, potassium, calcium, magnesium, lithium, aluminum, zinc, etc. The salts can be prepared by treatment of a compound of formula I with a sufficient amount of the desired base to give the salt in a conventional manner. The compounds of formula I and their salts differ in certain physical properties, such as solubility, but they are equivalent for the purposes of the invention.

Some compounds of the present invention can exist in solvated form, including hydrated forms. In general, the solvated forms, with pharmaceutically acceptable solvents such as water, ethanol and the like, are equivalent to the unsolvated form for the purposes of the invention.

Some compounds of the present invention can exist as various diastereoisomers and/or optical isomers. Diastereoisomers can be separated by conventional techniques such as chromatography or fractional crystallization. The optical isomers can be resolved using conventional techniques of optical resolution, to give the optically pure isomers. This resolution can be performed upon any chiral synthetic intermediate or upon the products of general formula I. The optically pure isomers can also be individually obtained using enantiospecific synthesis. The present invention covers both the individual isomers and the mixtures (for example racemic mixtures), whether obtained by synthesis or by physically mixing them up.

Furthermore, some of the compounds of the present invention may exhibit cis/trans isomery. Geometric isomers can be separated by conventional techniques such as chromatography or recrystallization. Such a separation can be performed either upon the products of formula I or upon any synthetic intermediate thereof. The individual isomers can also be obtained using stereospecific synthesis. The present invention covers each of the geometric isomers and the mixtures thereof.

The present invention also provides a process for preparing the compounds of formula I. As it will be obvious to a person skilled in the art, the precise method used for the preparation of a given compound can vary depending on its chemical structure. Furthermore, in most of the processes that are described below it may be necessary or appropriate to protect the reactive or labile groups using conventional protecting groups. Both the nature of said protecting groups and the processes for their introduction and removal are well known and belong to the state of the art (see for example Greene T. W. and Wuts P. G. M., "Protective Groups in Organic Synthesis", 3$^{rd}$ Edition, John Wiley & Sons, 1999). For example, carboxyl groups can be protected as $C_{1-4}$ alkyl esters, such as methyl, ethyl or tert-butyl ester, or aryl$C_{1-4}$ alkyl esters, such as benzyl ester. Whenever a protecting group is present, a subsequent deprotection step will be necessary, which can be performed under standard conditions in organic chemistry such as those described in the reference mentioned above.

The compounds of formula I can be obtained in general by alkylation of a phenol of formula II

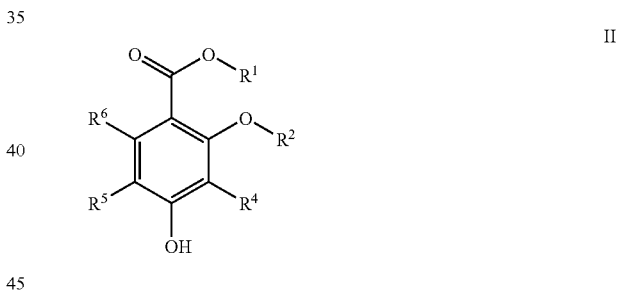

wherein $R^1$, $R^2$, $R^4$, $R^5$ and $R^6$ have the meaning described above, with an alkylating agent of formula G-$R^3$ (III), wherein $R^3$ has the meaning described above and G represents a leaving group such as a halogen atom, for example chloro, bromo or iodo, or an alkyl-, haloalkyl- or arylsulfonate, such as for example mesylate, tosylate, 2,4,6-trimethylbenzenesulfonate or trifluoromethanesulfonate. The reaction is carried out in the presence of a suitable base for the deprotonation of the phenol, such as sodium, potassium or cesium carbonate, sodium or potassium hydroxide, sodium hydride, sodium or potassium tert-butoxide, or n-butyllithium, in a suitable solvent. Examples of suitable solvents include, among others, dimethyl sulfoxide, tetrahydrofuran, tetrahydrofuran-hexamethylphosphoramide mixtures and substituted amides such as for example dimethylformamide, dimethylacetamide and N-methyl-2-pyrrolidinone. The reaction is carried out at a temperature preferably comprised between 0° C. and the temperature of the boiling point of the solvent.

Alternatively, when in a compound of formula II $R^1$ and $R^2$ represent hydrogen, that is in case of a compound of formula IIa

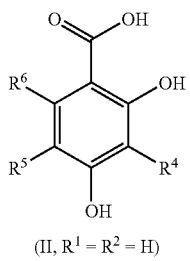

(II, $R^1 = R^2 = H$)

the reaction can also be carried out in addition in the presence of a Lewis acid in the reaction medium. The process comprises the treatment of a compound of formula IIa in deprotonated form with said Lewis acid and subsequent addition of the alkylating agent to the reaction medium. Examples of suitable Lewis acids to carry out the reaction include, among others, a trialkylborate such as trimethylborate or triethylborate, metallic halides such as iron(III) chloride, magnesium bromide or zinc bromide, and trimethylsilyl chloride.

Alternatively, the compounds of the present invention can also be obtained by interconversion from another compound of formula I, in one or more steps, using standard reactions in organic chemistry.

For example, a $R^1$ group can be converted into another $R^1$ group, by conversion of a carboxylic acid into an ester. Such esterification can be carried out under standard conditions for the esterification of carboxylic acids, well known to those skilled in the art. Thus, for example, a compound of formula I as a carboxylic acid ($R^1$=H) can be reacted with an alcohol of formula HO—$R^1$ (IV), wherein $R^1$ represents $C_{1-4}$ alkyl, in the presence of a catalytic amount of a mineral acid such as for example sulfuric acid. Furthermore, a reactive derivative of said acid, such as the acyl halide, can be reacted with an alcohol of formula IV, in the presence of a weak base such as triethylamine or diisopropylethylamine. Alternatively, the carboxylic acid can be activated in situ using a suitable activating agent such as a carbodiimide, for example N,N'-dicyclohexylcarbodiimide or N-[3-(dimethylamino)propyl]-N'-ethylcarbodiimide, in the presence of a base such as dimethylaminopyridine, triethylamine or diisopropylethylamine, and in the presence of a suitable solvent such as a halogenated hydrocarbon, for example dichloromethane or chloroform, or a substituted amide such as dimethylformamide.

Furthermore, a group $R^2$ can be converted into another group $R^2$ by transformation of a group —OH($R^2$=H) into a group —OC(=O)$R^7$ ($R^2$=—C(=O)$R^7$). Said reaction can be carried out under the standard conditions for the formation of esters mentioned above, preferably by reacting a compound of formula I wherein $R^2$ represents hydrogen with an anhydride of formula [$R^7$C(=O)]$_2$O, or with the corresponding acyl halide, in the presence of a suitable base. Suitable bases to carry out said reaction include pyridine, or triethylamine or diisopropylethylamine in the presence of a suitable solvent such as a halogenated solvent, for example chloroform or dichloromethane.

Likewise, the compounds of formula I wherein $R^1$ represents $C_{1-4}$ alkyl and/or wherein $R^2$ represents —C(=O)$R^7$ can be converted into other compounds of formula I wherein $R^1$ and/or $R^2$ represent hydrogen by hydrolysis of the corresponding ester bonds. The hydrolysis of said function can be carried out in the presence of a base such as potassium hydroxide or lithium hydroxide, in the presence of a suitable solvent such as a polar solvent, for example methanol, ethanol, tetrahydrofuran, methanol-water mixtures, ethanol-water mixtures or tetrahydrofuran-water mixtures, or an a polar solvent such as benzene in the presence of a crown ether, for example 18-C-6.

The phenols of formula II and the alkylating agents of formula III used for the preparation of the compounds of formula I are either commercially available, widely described in the literature or can be prepared by methods analogous to those described starting from commercially available products and using standard methods in organic chemistry, well known to those skilled in the art.

Thus, for example, certain starting phenols of formula II which are not commercially available can be obtained by esterification and/or acylation of 2,4-dihydroxybenzoic acid, which is commercially available. These reactions are carried out according to the methods described above for the esterification and acylation of the compounds of formula I.

The alkylating agents of formula III can be commercially available, or when the leaving group G is an alkylsulfonate, haloalkylsulfonate or arylsulfonate can be obtained by reaction of an anhydride of the corresponding alkylsulfonic, haloalkylsulfonic or arylsulfonic acid with an alcohol of formula HO—$R^3$ (V), wherein $R^3$ has the meaning described above. Furthermore, they can also be obtained by reaction of the chloride of the corresponding alkyl-, haloalkyl- or arylsulfonic acid with said alcohols, in the presence of a base such as pyridine, or diisopropylethylamine or triethylamine in the presence of a suitable solvent such as for example a halogenated hydrocarbon, such as dichloromethane or chloroform.

Likewise, alcohols of formula V can be commercially available or can be obtained from other commercially available compounds by well known methods in organic chemistry.

Finally, the salts of the compounds of formula I can be prepared by conventional methods, for example by treatment with a base such as sodium hydroxide or potassium hydroxide.

As mentioned above, the compounds of formula I show immunomodulating activity and therefore they are useful for the treatment or prevention of immune diseases. Examples of immune diseases which can be treated or prevented with the compounds of the invention include, among others, psoriasis, other skin diseases such as atopic dermatitis, contact dermatitis, lichen planus, dermatomyositis, scleroderma, erythema multiform, urticaria and pemphigus, inflammatory bowel disease including Crohn's disease and ulcerative colitis, rheumatoid arthritis and other arthritic diseases such as gouty arthritis, psoriatic arthritis, juvenile arthritis and ankylosing spondylitis, multiple sclerosis and other autoimmune neuropathies, diabetes, transplant rejection, graft-versus-host disease, lupus erythematosus, vasculitis, Sjögren's syndrome, Guillain-Barre syndrome, glomerulonephritis, respiratory diseases such as allergic rhinitis, asthma, fibrosis and chronic obstructive pulmonary disease, and neoplasias with proliferation of immune cells.

Moreover, the compounds of formula I exhibit apoptosis-inducing activity in cancer cells and may therefore be used also for the treatment or prevention of cancer. Throughout the present description the terms neoplasia and cancer are used indistinctively. Illustrative cancers that may be treated by the compounds of the present invention include, but are not limited to, lung cancer, colon cancer, central nervous system cancers, melanoma, ovarian cancer, prostate cancer, breast cancer, lymphomas, leukemias, esophageal cancer, stomach cancer and liver cancer.

According to the activity of, the products herein described, the present invention also relates to compositions which comprise a compound of the present invention (or a pharmaceutically acceptable salt, solvate or prodrug thereof), together with an excipient or other auxiliary agents if necessary. The compounds of the present invention have shown activity both when administered topically or systemically. Therefore, any administration route may in principle be used for these products, for example topical, oral, parenteral or rectal administration.

Formulations for topical administration include creams, ointments, lotions, gels, powders, solutions and patches wherein the compound is dispersed or dissolved in suitable excipients, which in addition can facilitate its topical absorption, such as diisopropyl myristate or diisopropyl adipate, octyidodecanol, polyethylene glycols and diethylene glycol monoethyl ether, among others.

The compound can be incorporated in a suitable ointment using a hydrophilic oily base such as for example polyethylene glycols or a hydrophobic oily base such as for example paraffin or mineral oil with polyethylene.

Formulations in the form of emulsions such as creams and lotions comprise an oily phase (5-40%), an aqueous phase and an emulgent. For the oily phase any excipient commonly-used in this type of formulations may be used. The compound will be incorporated into the aqueous phase or the oily phase depending on the excipient or excipients used to dissolve or disperse it. The choice of the emulgent will be conditioned by the type of emulsion: if an external aqueous phase (o/w emulsion) is used, an emulgent such as for example cetomacrogol or glycol stearate can be used, among others, while if an external oily phase is used (w/o emulsion) an emulgent such as sorbitan tristearate or sorbitan monoisostearate can be used, among others. Depending on the resulting viscosity, the pharmaceutical form will be a cream (semisolid consistence) or a lotion (liquid consistence).

Furthermore, the compound can also be incorporated into a gel, structural network of a hydrophilic colloid, such as for example carbomer.

All these topical compositions can additionally contain auxiliary excipients such as emolients, buffers, preservatives, antioxidants and perfuming agents.

Furthermore, the compound can also be administered for topical use in a vector system using liposomes, nanoemulsions or nanocapsules.

Solid compositions for oral administration include tablets, granulates and capsules. In any case the manufacturing method is based on a simple mixture, dry granulation or wet granulation of the active compound with excipients. These excipients can be, for example, diluents such as lactose, microcrystalline cellulose, mannitol or calcium hydrogenphosphate; binding agents such as for example starch, gelatin or povidone; disintegrants such as sodium carboxymethyl starch or sodium croscarmellose; and lubricating agents, such as for example magnesium stearate, stearic acid or talc. Tablets can be additionally coated with suitable excipients by using known techniques with the purpose of delaying their disintegration and absorption in the gastrointestinal tract and thereby provide a sustained action over a longer period, or simply to improve their organoleptic properties or their stability. The active compound can also be incorporated by coating onto inert pellets using natural or synthetic film-coating agents. Soft gelatin capsules are also possible, wherein the active compound is mixed with water or an oily medium, for example coconut oil, mineral oil, or olive oil.

Powders and granulates for the preparation of oral suspensions by the addition of water can be obtained by mixing the active compound with dispersing or wetting agents; suspending agents and preservatives. Other excipients can also be added, for example sweetening, flavouring and colouring agents.

Liquid forms for oral administration include emulsions, solutions, suspensions, syrups and elixirs containing commonly-used inert diluents, such as purified water, ethanol, sorbitol, glycerol, polyethylene glycols (macrogols) and propylene glycol. Said compositions can also contain coadjuvants such as wetting, suspending, sweetening, flavouring agents, preservatives and buffers.

Injectable preparations, according to the present invention, for parenteral administration comprise sterile solutions, suspensions or emulsions, in an aqueous or non-aqueous solvent such as propylene glycol, polyethylene glycol or vegetable oils. These compositions can also contain coadjuvants, such as wetting, emulsifying, dispersing agents and preservatives. They may be sterilized by any known method or prepared as sterile solid compositions to be dissolved in water or any other sterile injectable medium immediately before use. It is also possible to start from sterile materials and keep them under these conditions throughout all the manufacturing process.

For the rectal administration, the active compound can be preferably formulated as a suppository on an oily base, such as for example vegetable oils or solid semisynthetic glycerides, or on a hydrophilic base like polyethylene glycols (macrogols).

The dose of a compound of formula I to be administered and the frequency of doses will depend upon a variety of factors such as the nature and severity of the disease to be treated, the age and body weight of the patient, as well as the route of administration. In human therapy the daily dose for an adult when a compound of formula I is administered orally will generally be comprised between 0.1 and 100 mg/kg/day, which can be administered as a single or divided doses. When the compound of formula I is administered topically, in general it will be administered at a concentration in the range 0.01-10%. As it will be evident to those skilled in the art, however, in special cases or depending on the nature or severity of the disease to be treated doses outside these margins might be necessary. A person skilled in the art will be able to readily determine the suitable dose for each situation without undue experimentation.

The compounds of the present invention can be administered either as single agents or, alternatively, in combination with one or more drugs known to be useful for the treatment or prevention of the disease that it is desired to treat or prevent. Said combination products can be adapted for the simultaneous (including the administration in a single dose unit), sequential or separate administration of the active ingredients.

In particular, when the compounds of the invention are used for the treatment or prevention of cancer, they can be administered in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrix metalloprotease inhibitors, telomerase inhibitors, tyrosine kinase inhibitors, antigrowth factor receptor agents, anti-HER agents, anti-EGFR agents, anti-angiogenesis agents, farnesyl transferase inhibitors, ras-raf signal transduction pathway inhibitors, cell cycle inhibitors, cdks inhibitors, tubulin binding agents, topoisomerase I inhibitors, topoisomerase II inhibitors, and the like.

As an example, the compounds of the invention can be administered in combination with one or more chemotherapeutic agents such as, for instance, aldesleukin, alemtuzumab, anastrozole, anthracycline glycosides (e.g. doxorubicin, idarubicin, epirubicin, valrubicin and daunorubicin), arsenic trioxide, asparaginase, bexarotene, bicalutamide, bleomycin, busulfan, camptothecins, capecitabine, carboplatin, carmustine, celecoxib, chlorambucil, cisplatin, cladribine, cyclophosphamide, cytarabine, dacarbazine, dactinomycin, denileukin diftitox, etoposide, exemestane, floxuridine, fludarabine, 5-fluorouracil, flutamide, gemcitabine, gemtuzumab ozogamicin, hydroxyurea, ifosfamide, imatinib, interferon alfa, irinotecan, letrozole, leuprolide, lomustine, mechlorethamine, megestrol, melphalan, mercaptopurine, methotrexate, mitomycin, mitotane, mitoxantrone, nilutamide, oxaliplatin, pegaspargase, pentostatin, plicamycin, procarbazine, rituximab, streptozocin, tamoxifen, taxanes (e.g. paclitaxel, docetaxel), temozolomide, teniposide, testolactone, thioguanine, thiotepa, topotecan, toremifene, trastuzumab, triptorelin, vinblastine, vincristine, vindesine, vinorelbine and the like.

In said combination products, the compounds of this invention are administered in general within the dosage ranges described above while the other pharmaceutically active agent(s) are administered within the dosage ranges commonly used in therapy, which will be well known to those skilled in the art.

Accordingly, the present invention also provides a product comprising a compound of formula I (or a pharmaceutically acceptable salt, solvate or prodrug thereof) and one or more additional drugs as a combined preparation for simultaneous, sequential or separate use. In a preferred embodiment, such product comprises a compound of formula I and one or more chemotherapeutic agents.

The invention also provides a pharmaceutical composition which comprises a compound of formula I (or a pharmaceutically acceptable salt, solvate or prodrug thereof), one or more additional drugs and one or more pharmaceutically acceptable excipients. In a preferred embodiment, such pharmaceutical composition comprises a compound of formula I (or a pharmaceutically acceptable salt, solvate or prodrug thereof), one or more chemotherapeutic agents and one or more pharmaceutically acceptable excipients.

The following examples illustrate the present invention and are not to be construed as limiting the scope of the invention in any way.

The following abbreviations have been used in the examples:
Ac$_2$O: acetic anhydride
AcOH: acetic acid
DMF: dimethylformamide
EtOAc: ethyl acetate
MeOH: methanol

EXAMPLE 1

Methyl 2-hydroxy-4-(2,2,3,3,3-pentafluoropropoxy)benzoate a) 2,2,3,3,3-Pentafluoropropyl tosylate To a solution of 2,2,3,3,3-pentafluoropropanol (5.0 mL, 50 mmol) and pyridine (8.1 mL, 100 mmol) in chloroform (100 mL), cooled at 0° C. and under argon, tosyl chloride (14.29 g, 75 mmol) was slowly added. The resulting mixture was allowed to warm up to room temperature and was stirred at this temperature overnight. Then, 10% aqueous K$_2$CO$_3$ solution was added and the mixture was vigorously stirred for 30 min. The layers were separated, and the organic layer was treated again with K$_2$CO$_3$. After that, it was washed with 2 N HCl, dried over Na$_2$SO$_4$ and the solvent was removed, yielding 12.72 g of the desired compound (84% yield).

$^1$H NMR (300 MHz, CDCl$_3$) δ (TMS): 2.47 (s, 3 H), 4.41 (t, J=12.3 Hz, 2 H), 7.39 (d, J=8.4 Hz, 2 H), 7.81 (d, J=8.4 Hz, 2 H).

b) Title Compound

A mixture of methyl 2,4-dihydroxybenzoate (5.04 g, 30 mmol) and K$_2$CO$_3$ (4.56 g, 33 mmol) in DMF (30 mL) was heated under argon at 50° C. for some minutes. It was cooled to room temperature, 2,2,3,3,3-pentafluoropropyl tosylate (10.03 g, 33 mmol, obtained in the preceding section) was added and the resulting mixture was stirred at 50° C. overnight, at 80° C. for 6 hours and finally at 50° C. for 3 days. The mixture was allowed to cool to room temperature and was acidified with 6 N HCl. The resulting mixture was extracted with EtOAc (×4), and the combined organic layers were washed with H$_2$O and brine. The organic layer was dried over Na$_2$SO$_4$ and concentrated to dryness. The crude product obtained was purified by chromatography on silica-gel using hexane-EtOAc mixtures of increasing polarity as eluent, yielding the title compound as a white solid.

$^1$H NMR (300 MHz, CDCl$_3$) δ (TMS): 3.94 (s, 3H), 4.43 (t, J=12.1 Hz, 2H), 6.49 (complex signal, 2 H), 7.79 (d, J=8.5 Hz, 1 H), 10.99 (s, 1 H).

Following a similar procedure to that described in sections a and b of example 1, but starting in each case from a suitable alcohol for the preparation of the corresponding intermediate of step a, the following compounds were obtained:

EXAMPLE 2

Methyl 2-hydroxy-4-(2,2,2-trifluoroethoxy)benzoate

Starting alcohol: 2,2,2-trifluoroethanol
M.p.=78-79° C.
$^1$H NMR (300 MHz, CDCl$_3$) δ (TMS): 3.94 (s, 3H), 4.38 (q, J=8.0 Hz, 2H), 6.50 (complex signal, 2 H), 7.81 (d, J=8.8 Hz, 1 H), 11.00 (s, 1 H).

EXAMPLE 3

Methyl 2-hydroxy-4-(2,2,3,3-tetrafluoropropoxy)benzoate

Starting alcohol: 2,2,3,3-tetrafluoropropanol
M.p.=224° C.
$^1$H NMR (300 MHz, CDCl$_3$) δ (TMS): 3.93 (s, 3H), 4.39 (t, J=10.4 Hz, 2H), 6.04 (tt, J$_{gem}$=53.1 Hz, J$_{vic}$=4.7 Hz, 1 H), 6.48 (complex signal, 2 H), 7.79 (d, J=9.5 Hz, 1 H), 10.98 (s, 1 H).

EXAMPLE 4

Methyl 2-hydroxy-4-(2-fluoroethoxy)benzoate

Starting alcohol: 2-fluoroethanol
M.p.=64° C.
$^1$H NMR (300 MHz, CDCl$_3$) δ (TMS): 3.98 (s, 3 H), 4.29 (d of m, $J_{H-F}$=27.7 Hz, 2H), 4.82 (d of m, $J_{H-F}$=47.3 Hz, 2H), 6.51 (s, 1 H), 6.53 (d, J=8.7 Hz, 1 H), 7.81 (d, J=8.7 Hz, 1 H), 11.04 (s, 1 H).

EXAMPLE 5

Methyl 4-(2,2-difluoroethoxy)-2-hydroxybenzoate

Starting alcohol: 2,2-difluoroethanol
$^1$H NMR (300 MHz, CDCl$_3$) δ (TMS): 3.93 (s, 3H), 4.19 (td, $J_{H-F}$=12.9 Hz, $J_{H-H}$=4.1 Hz, 2 H), 6.09 (tt, $J_{H-F}$=54.9 Hz, $J_{H-H}$=4.1 Hz, 1H), 6.47 (complex signal, 2 H), 7.77 (d, J=8.9 Hz, 1 H), 10.98 (s, 1 H).

EXAMPLE 6

2-Hydroxy-4-(2,2,3,3,3-pentafluoropropoxy)benzoic acid

Method A a) 2,2,3,3,3-Pentafluoropropyl trifluoromethanesulfonate

A mixture of trifluoromethanesulfonic anhydride (40 mL, 0.24 mol) and 2,2,3,3,3-pentafluoropropanol (25 mL, 0.24 mol) was heated under argon at 90° C. overnight. Then, the crude mixture was distilled at atmospheric pressure to give the desired product as a colourless oil (97% yield).
$^1$H NMR (200 MHz, CDCl$_3$) δ (TMS): 4.78 (t, J=11.7 Hz, 2 H).

b) Title Compound

To a mixture of 95% NaH (1.43 g, 56.64 mmol) in DMF (12 mL) under argon, a solution of 2,4-dihydroxybenzoic acid (3.00 g, 18.88 mmol) in DMF (18 mL) was added. The resulting suspension was stirred at room temperature for 30 min. Next, B(OCH$_3$)$_3$ (6.3 mL, 56.64 mmol) was added dropwise and the reaction mixture was stirred for one hour more at room temperature. Then, the compound obtained in the preceding section (5.0 mL, 28.32 mmol) was added dropwise and the resulting mixture was stirred at 100° C. overnight. The mixture was cooled to room temperature and acidified with 1 N HCl to pH 1. The solution thus obtained was extracted with EtOAc and the organic phase was washed with H$_2$O and brine, dried over Na$_2$SO$_4$ and concentrated to dryness. The crude product obtained was recrystallized in AcOH (4 times, 3 mL AcOH each time), affording the title compound as a slightly coloured solid (66% yield).
M.p.=147-148° C.
$^1$H NMR (200 MHz, CDCl$_3$) δ (TMS): 4.42 (t, J=12.4 Hz, 2H), 6.45 (d, J=2.2 Hz, 1 H), 6.50 (d, J=2.6 Hz, 1 H), 7.82 (d, J=8.4 Hz, 1 H).

Method B:

To a solution of methyl 2-hydroxy-4-(2,2,3,3,3-pentafluoropropoxy)benzoate (obtained in example 1) (0.72 g, 2.40 mmol) in MeOH (9.7 mL), KOH (0.51 g, 86%; 7.80 mmol) dissolved in H$_2$O (3 mL) was added and the resulting mixture was refluxed for 4 hours. The mixture was allowed to cool and MeOH was evaporated. The residue thus obtained was treated with H$_2$O (5 mL) and the resulting solution was acidified with 6 N HCl. The white solid formed was collected by filtration, washed with cold H$_2$O and dried in vacuo, yielding the title compound (55% yield).

Following a similar procedure to that described in method B of example 6, and starting in each case from the suitable ester, the following compounds were obtained:

EXAMPLE 7

2-Hydroxy-4-(2,2,2-trifluoroethoxy)benzoic acid

Starting ester: methyl 2-hydroxy-4-(2,2,2-trifluoroethoxy)benzoate (obtained in example 2)
M.p.=177-179° C.
$^1$H NMR (300 MHz, CD$_3$OD) δ (TMS): 4.63 (q, J=8.4 Hz, 2H), 6.61 (complex signal, 2 H), 7.87 (d, J=8.1 Hz, 1 H).

EXAMPLE 8

2-Hydroxy-4-(2,2,3,3-tetrafluoropropoxy)benzoic acid

Starting ester: methyl 2-hydroxy-4-(2,2,3,3-tetrafluoropropoxy)benzoate (obtained in example 3)
M.p.=145-151° C.
$^1$H NMR (300 MHz, CDCl$_3$+CD$_3$OD) δ (TMS): 4.39 (t, J=12.1 Hz, 2H), 6.12 (tt, $J_{gem}$=52.8 Hz, $J_{vic}$=4.9 Hz, 1 H), 6.47 (complex signal, 2 H), 7.80 (d, J=8.6 Hz, 1 H).

EXAMPLE 9

2-Hydroxy-4-(2-fluoroethoxy)benzoic acid

Starting ester: methyl 2-hydroxy-4-(2-fluoroethoxy)benzoate (obtained in example 4)
M.p.=160° C.
$^1$H NMR (300 MHz, CD$_3$OD) δ (TMS): 4.22 (d of m, $J_{H-F}$=28.8 Hz, 2 H), 4.71 (d of m, $J_{H-F}$=47.7 Hz, 2H), 6.47 (complex signal, 2 H), 7.76 (d, J=8.7 Hz, 1 H).

EXAMPLE 10

4(2,2-Difluoroethoxy)-2-hydroxybenzoic acid

Starting ester: methyl 4-(2,2-difluoroethoxy)-2-hydroxybenzoate (obtained in example 5)
M.p.=154-163° C.
$^1$H NMR (300 MHz, CD$_3$OD) δ (TMS): 4.31 (td, $J_{H-F}$=13.7 Hz, $J_{H-H}$=3.8 Hz, 2 H), 6.22 (tt, $J_{H-F}$=54.8 Hz, $J_{H-H}$=3.8 Hz, 1H), 6.55 (complex signal, 2 H), 7.84 (d, J=8.6 Hz, 1 H).

EXAMPLE 11

2-Acetoxy-4-(2.2,3,3,3-pentafluoropropoxy)benzoic acid

A solution of 2-hydroxy-4-(2,2,3,3,3-pentafluoropropoxy) benzoic acid (obtained in example 6) (0.45 g, 1.6 mmol) in pyridine (3 mL) was cooled to 0° C. and Ac$_2$O (0.25 mL) was added. The resulting mixture was stirred for 15 min at 0° C. and for 2 h at room temperature. The mixture was then concentrated and the residue was treated with H$_2$O (10 mL) and stirred until precipitation (2 h). The solid was collected by filtration and was purified by chromatography on silica-gel using hexane-EtOAc mixtures of increasing polarity as eluent, to afford 0.2 g of the desired product as a white solid (38% yield).

M.p.=126° C.

$^1$H NMR (300 MHz, CD$_3$OD+CDCl$_3$) δ (TMS): 2.29 (s, 3 H), 4.52 (t, J=12.7 Hz, 2 H), 6.70 (d, J=2.5 Hz, 1 H), 6.90 (d, J=8.8 Hz, 1 H), 8.01 (d, J=8.8 Hz, 1 H).

EXAMPLE 12

2-Acetoxy-4-(2-fluoroethoxy)benzoic acid

Following a similar procedure to that described in example 11, but using 2-hydroxy-4-(2-fluoroethoxy)benzoic acid (obtained in example 9) instead of 2-hydroxy-4-(2,2,3,3,3-pentafluoropropoxy)benzoic acid, the title compound was obtained.

M.p.=126-127° C.

$^1$H NMR (300 MHz, CDCl$_3$) δ (TMS): 2.34 (s, 3 H), 4.28 (d, J=25.1 Hz, 2 H), 4.77 (d, J=47.3 Hz, 2 H), 6.67 (d, J=2.5 Hz, 1 H), 6.87 (d, J=8.9 Hz, 1 H), 8.09 (d, J=8.9 Hz, 1 H).

The utility of the compounds of the present invention for the treatment or prevention of psoriasis and other immune diseases as well as for the treatment or prevention of cancer can be shown using the following pharmacological tests:

Test 1—Oxazolone-induced Delayed Hipersensitivity in Mice

Method: Male Swiss mice (25-30 g body weight) were sensitized by the application of a 2% solution of oxazolone (Sigma) in acetone (50 μL) into the shaved abdomen. Seven days later, 25 μL of a 1.5% solution of oxazolone was applied on both surfaces of the right ear of the animals. The left ear served as control and was only treated with the vehicle (acetone). 20 μL of the test compound (dissolved in acetone) or vehicle alone (control) was applied on both sides of the right ear, 24 h before challenge and 1 and 5 h after challenge. To evaluate the edema, mice were killed (by CO$_2$ inhalation) and an 8 mm disc was excised from the right and left ears. The edema was measured by the difference in weight between the two ears and inhibition was expressed as percentage in relation to the control group.

Results: The results obtained with the compound of example 6 are shown in FIG. 1. It can be observed that this compound produced a concentration-dependent inhibition of the edema. Similar results are obtained when the product of example 6 is administered as an ointment (obtained by dissolving the product in diethylene glycol monoethyl ether and incorporating it into the base excipient YR-24461®) instead of as a solution in acetone.

Test 2—Psoriasis Model in Immune-deficient BNX Mice Transplanted with Human Psoriatic Skin Method: The goal of this study is to assess the effect of the test compounds on the development of a psoriatic lesion, induced by super-antigen-activated human peripheral blood T-cells, in non-lesional skin from a psoriasis patient transplanted onto immune-deficient BNX mice. Mice (male/female, circa 20 g, 5 mice per group) were transplanted with non-lesional skin biopsies from psoriasis patients. Peripheral blood mononuclear cells from the same patients were isolated and stored in freezer until further use. Transplants were allowed to "lake" for 4 weeks. After this period, transplants were treated topically with test compound or control (vehicle) preparations for 1 week. Then, peripheral blood mononuclear cells from psoriatic patients, previously activated in vitro for 2 days with super-antigen, were injected into the transplants intra-dermally. Transplants were treated with test compound or control preparations for two additional weeks. Transplants were then harvested and epidermal thickness was measured by using computer-aided morphometric analysis.

Results: The compound of example 6, administered as an ointment (obtained as described in test 1) at the concentration of 0.1%, produced a significant inhibition (p<0.01) of the increase of the epidermal thickness induced by intradermal injection of activated mononuclear cells.

Test 3—Inhibition of Adjuvant-induced Arthritis in the Rat

Method: Male Lewis rats with body weight between 140 and 170 g and 7 week-old were used. Before the start of the study animals were acclimated for a period of at least 5 days. Animals were fasted for 18 hours before the study, with water ad libitum. Throughout the study, animals were allowed free access to drinking water, except during observation periods.

Groups of five animals were randomized (Sham, Control and Test compound). The duration of the study was 28 days. Arthritis was induced on day 1 of the study by a single subplantar injection of 0.1 mL of an emulsion prepared with 10 mg *Mycobacterium butyricum* and 10 mL Freund's incomplete adjuvant (Difco) to the right hindpaw of the animals from the Control (C) and Test compound (T) groups. Sham animals (S) received 0.1 mL Freund's incomplete adjuvant. Test compound was administered daily from day 1 of the study until day 28 at a dose of 10 mg/kg p.o. as a suspension in 1% Tween 80® while the Control group only received the vehicle. On day 28 of the development of arthritis, the volume of the left paw (secondary edema) was determined using a UGO BASILE 7150 plethysmometer. The inhibition of the increase in volume was calculated as follows:

$$\% \text{ Inh.}=100-((T-S)/(C-S))*100$$

Where: T=Test compound group; C=Control group; and S=Sham group

Results: Oral administration of the compound of example 6 for 28 days at the dose of 10 mg/kg/day produced a significant inhibition of the increase in volume of immunological origin induced by *M. butyricum* and adjuvant in control animals.

Test 4—Immunosupression Model: Murine Mixed Lymphocyte Reaction

Method: Immunosuppression was assessed by testing the effects of the compounds on the proliferation of splenic lymphocytes from C57BL/6 mice strain stimulated with splenic lymphocytes from CBA mice strain. Splenic lymphocyte populations were isolated from two mouse strains: CBA (acting as stimulating cells) and C57BL/6 (acting as proliferating cells). Homogenized mouse spleen was filtered and subsequently centrifuged at 250×g for 5 minutes at 4° C. The pellets were resuspended in culture medium (RPMI 1640 supplemented with 5% fetal calf serum and 2% antibiotics) and after repeating this process twice they were adjusted to a final density of 5×10$^6$ cells/mL. The isolated lymphocytes from CBA strain were treated with mitomycin C to block their proliferation.

In a 96-well plate, solutions of the test compounds or culture medium alone (for the control) were distributed. Next, 5×10$^5$ C57BL/6 cells and 2.5×10$^5$ CBA cells were added and incubated for 48 h (37° C., 5% CO$_2$). After this preincubation 1 μCi of [$^3$H]-thymidine and 0.2 mM unlabeled thymidine were added to each well and the mixture was incubated 24 h.

After this period, the samples were transferred into a filter plate (Millipore) and the cells were washed 3 times with phosphate-buffered saline solution.

Lymphocyte proliferation was measured as [³H]-thymidine incorporation into the DNA of responding cells (C57BL/6) using a liquid scintillation counter (LS series, Beckman).

Results: The compound of example 6 at a concentration of 300 μM completely inhibited mice splenic lymphocyte proliferation. When administered at 100 μM, it gave 60% inhibition of the proliferation.

Similar results were obtained with the compound of example 6 in a human T-lymphocyte proliferation inhibition assay.

Test 5: Induction of Apoptosis in Tumor Cells

Method: The ability of the compounds of the invention to induce apoptosis was determined in a hamster lung fibroblast cell line (V79 cells). To determine the induction of apoptosis a commercially available kit was used (CaspaTag™ Caspase-3 (DEVD) Activity Kit, Intergen); this kit detects the presence in the cells of the active form of the enzyme caspase-3, which is an apoptosis marker. V79 cells were incubated for 72 h in culture medium (DMEM supplemented with 2 mM Glutamine and 10% fetal calf serum) in the presence of test compound (30 and 100 μM; solution in phosphate-buffered saline) or vehicle. Next, cells were washed with phosphate-buffered saline, treated with Trypsin-EDTA solution until the cell layer was dispersed and were resuspended in fresh growth medium at a concentration of 10⁶ cells/mL. A 300 μL aliquote of each of the samples was transferred to a tube and was incubated with the irreversible, carboxyfluorescein-labeled peptidic caspase-3 inhibitor FAM-DEVD-FMK for 1 hour at 37° C. in 5% $CO_2$ and protecting the tubes from light following the kit's instructions. This peptide binds covalently to the active form of caspase-3 but not to the inactive form of this enzyme. The inhibitor in excess was washed and the cells were then analyzed by flow cytometry at 488 nm.

Figure 2:
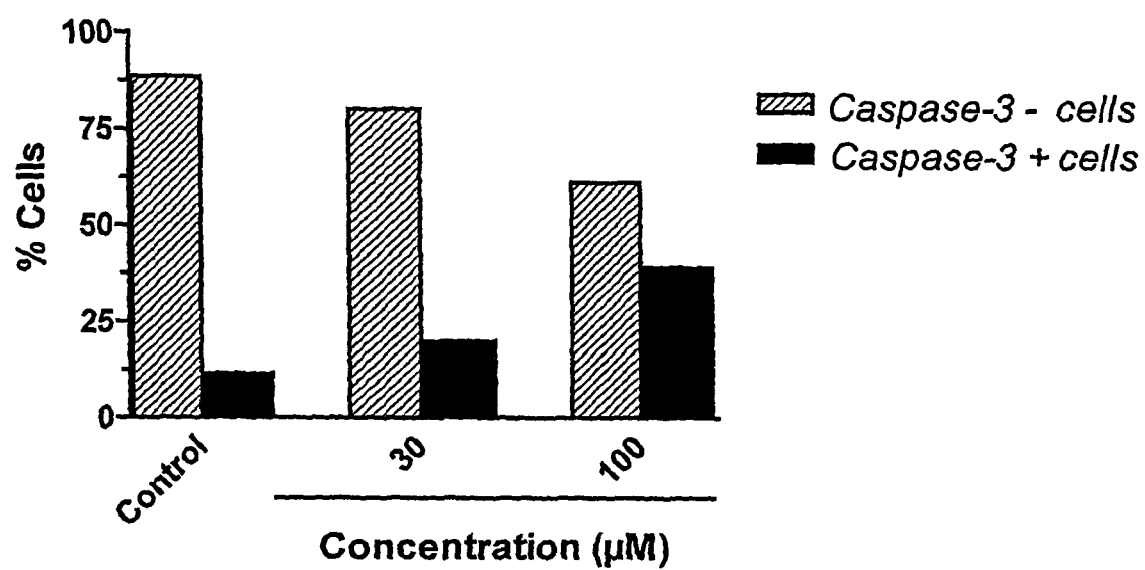
FIG. 2 is a bar chart showing the results obtained with the compound of Example 6 in the induction of apoptosis in tumor cells test (Test 5)

Results: The results obtained with the compound of example 6 at two different concentrations (30 and 100 μM) are shown in FIG. 2, where the percentage of apoptotic cells (active caspase-3 positive cells) and non-apoptotic cells (active caspase-3 negative cells) is depicted. Incubation of cells with the compound of example 6 produced a concentration-dependent increase in the number of cells containing the active form of caspase-3, thus showing the activation of the apoptotic process in these cells induced by said compound. This activation of apoptosis was also confirmed by morphological observation of the cells, which showed the presence of cell membrane blebbing and the formation of apoptotic bodies.

Moreover, the compound of example 6 was also shown not to affect cell viability in human non-proliferating cells, such as human peripheral blood mononuclear cells (PBMC) and human umbilical vein endothelial cells (HUVEC), at concentrations up to 500 μM and after 72 h of incubation.

The results of the preceding tests with a representative compound of the invention demonstrate the utility of the compounds of formula I in the treatment or prevention of psoriasis and other immune diseases, such as those mentioned above, as well as in the treatment or prevention of cancers.

The invention claimed is:

1. A compound of general formula I:

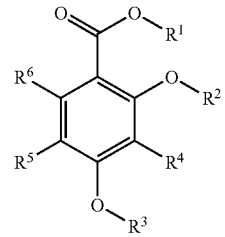

wherein:
$R^1$ represents hydrogen or $C_{1-4}$ alkyl;
$R^2$ represents hydrogen or —C(=O)$R^7$;
$R^3$ represents $C_{1-5}$ fluoroalkyl, $C_{2-5}$ fluoroalkenyl or $C_{2-5}$ fluoroalkynyl;
$R^4$, $R^5$ and $R^6$ independently represent hydrogen, $C_{1-4}$ alkyl, $C_{1-4}$ haloalkyl, $C_{1-4}$ alkoxy, $C_{1-4}$ haloalkoxy, halogen, cyano, hydroxy, nitro, —NR$^8$R$^9$, —S(O)$_x$R$^{10}$ or —C(=O)R$^{11}$;
$R^7$ and $R^{10}$ independently represent $C_{1-4}$ alkyl;
$R^8$, $R^9$ and $R^{11}$ independently represent hydrogen or $C_{1-4}$ alkyl; and
x represents 0, 1 or 2;
with the proviso that when $R^1$ represents methyl, $R^2$ represents hydrogen, $R^3$ represents 1,1,2,2-tetrafluoroethyl and $R^4$ and $R^5$ represent hydrogen then $R^6$ cannot be hydroxy, and with the further proviso that when $R^1$ represents hydrogen, $R^2$ represents hydrogen and $R^3$ represents 3-fluoropropyl then $R^4$, $R^5$ and $R^6$ cannot represent simultaneously fluoro;
or a salt thereof.

2. A compound according to claim 1 wherein $R^4$, $R^5$ and $R^6$ represent hydrogen.

3. A compound according to claim 1 or 2 wherein $R^3$ represents $C_{1-5}$ fluoroalkyl.

4. A compound according to claim 1 or 2 wherein $R^3$ represents $C_{1-3}$ fluoroalkyl, $C_{2-3}$ fluoroalkenyl or $C_{2-3}$ fluoroalkynyl.

5. A compound according to claim 1 or 2 wherein $R^3$ represents $C_{1-3}$ fluoroalkyl.

6. A compound according to claim 1 or 2 wherein $R^3$ represents 2,2,3,3,3-pentafluoropropyl.

7. A compound according to claim 1 or 2 wherein $R^1$ represents hydrogen.

8. A compound according to claim 1 or 2 wherein $R^2$ represents hydrogen or acetyl.

9. A compound according to claim 1 selected from:
methyl 2-hydroxy-4-(2,2,3,3,3-pentafluoropropoxy)benzoate;
methyl 2-hydroxy-4-(2,2,2-trifluoroethoxy)benzoate;
methyl 2-hydroxy-4-(2,2,3,3-tetrafluoropropoxy)benzoate;
methyl 2-hydroxy-4-(2-fluoroethoxy)benzoate;
methyl 4-(2,2-difluoroethoxy)-2-hydroxybenzoate;
2-hydroxy-4-(2,2,3,3,3-pentafluoropropoxy)benzoic acid;
2-hydroxy-4-(2,2,2-trifluoroethoxy)benzoic acid;
2-hydroxy-4-(2,2,3,3-tetrafluoropropoxy)benzoic acid;
2-hydroxy-4-(2-fluoroethoxy)benzoic acid;
4-(2,2-difluoroethoxy)-2-hydroxybenzoic acid;
2-acetoxy-4-(2,2,3,3,3-pentafluoropropoxy)benzoic acid; and
2-acetoxy-4-(2-fluoroethoxy)benzoic acid;
and a salt thereof.

10. 2-Hydroxy-4-(2,2,3,3,3-pentafluoropropoxy)benzoic acid or a salt thereof.

11. 2-Acetoxy-4-(2,2,3,3,3-pentafluoropropoxy)benzoic acid or a salt thereof.

12. A pharmaceutical composition which comprises an effective amount of a compound of formula I

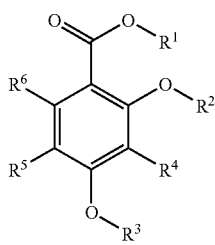

wherein:
- $R^1$ represents hydrogen or $C_{1-4}$ alkyl;
- $R^2$ represents hydrogen or —C(=O)$R^7$;
- $R^3$ represents $C_{1-5}$ fluoroalkyl, $C_{2-5}$ fluoroalkenyl or $C_{2-5}$ fluoroalkynyl;
- $R^4$, $R^5$ and $R^6$ independently represent hydrogen, $C_{1-4}$ alkyl, $C_{1-4}$ haloalkyl, $C_{1-4}$ alkoxy, $C_{1-4}$ haloalkoxy, halogen, cyano, hydroxy, nitro, —NR$^8$R$^9$, —S(O)$_x$R$^{10}$ or —C(=O)R$^{11}$;
- $R^7$ and $R^{10}$ independently represent $C_{1-4}$ alkyl;
- $R^8$, $R^9$ and $R^{11}$ independently represent hydrogen or $C_{1-4}$ alkyl; and
- x represents 0, 1 or 2;

with the proviso that when $R^1$ and $R^2$ each represents hydrogen, and $R^3$ represents 3-fluorophenyl, then $R^4$, $R^5$ and $R^6$ simultaneously cannot represent fluoro;

and with the further proviso that when $R^1$ represents methyl, $R^2$ represents hydrogen, $R^3$ represents 1,1,2,2-tetrafluoroethyl and $R^4$ and $R^5$ represent hydrogen then $R^6$ cannot be hydroxy, or a pharmaceutically acceptable salt thereof and one or more pharmaceutically acceptable excipients.

13. Process for preparing a compound of claim 1 which comprises (a) reacting a phenol of formula II

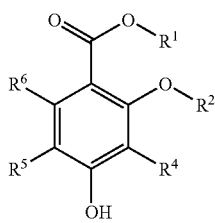

wherein $R^1$, $R^2$, $R^4$, $R^5$ and $R^6$ have the meaning described above, with an alkylating agent of formula G-$R^3$ (III), wherein $R^3$ has the meaning described above and G represents a leaving group; or (b) converting a compound of formula I into another compound of formula I; and (c) optionally, after the above steps and when $R^1$ and/or $R^2$ represent hydrogen, reacting a compound of formula I with a base, to obtain the corresponding addition salt.

14. A compound of general formula I:

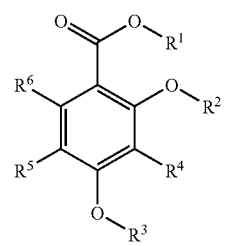

wherein:
- $R^1$ represents hydrogen or $C_{1-4}$ alkyl;
- $R^2$ represents hydrogen or —C(=O)$R^7$;
- $R^3$ represents $C_{1-5}$ fluoroalkyl, $C_{2-5}$ fluoroalkenyl or $C_{2-5}$ fluoroalkynyl;
- $R^4$, $R^5$ and $R^6$ independently represent hydrogen, $C_{1-4}$ alkyl, $C_{1-4}$ haloalkyl, $C_{1-4}$ alkoxy, $C_{1-4}$ haloalkoxy, halogen, cyano, hydroxy, nitro, —NR$^8$R$^9$, —S(O)$_x$R$^{10}$ or —C(=O)R$^{11}$;
- $R^7$ and $R^{10}$ independently represent $C_{1-4}$ alkyl;
- $R^8$, $R^9$ and $R^{11}$ independently represent hydrogen or $C_{1-4}$ alkyl; and
- x represents 0, 1 or 2;

with the proviso that when $R^1$ represents methyl, $R^2$ represents hydrogen, $R^3$ represents 1,1,2,2-tetrafluoroethyl and $R^4$ and $R^5$ represent hydrogen then $R^6$ cannot be hydroxy, and with the further proviso that when $R^1$ represents hydrogen, $R^2$ represents hydrogen and $R^3$ represents 3-fluoropropyl then $R^4$, $R^5$ and $R^6$ cannot represent simultaneously fluoro.

15. 2-Hydroxy-4-(2,2,3,3,3-pentafluoropropoxy)benzoic acid.

* * * * *

UNITED STATES PATENT AND TRADEMARK OFFICE
CERTIFICATE OF CORRECTION

| | | |
|---|---|---|
| PATENT NO. | : 7,589,125 B2 | Page 1 of 1 |
| APPLICATION NO. | : 10/521461 | |
| DATED | : September 15, 2009 | |
| INVENTOR(S) | : Bartrolí Orpí et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 591 days.

Signed and Sealed this

Twenty-first Day of September, 2010

David J. Kappos
*Director of the United States Patent and Trademark Office*